United States Patent [19]

Iwasaki et al.

[11] Patent Number: 4,540,838
[45] Date of Patent: Sep. 10, 1985

[54] PROCESS FOR PRODUCING CHLOROPRENE

[75] Inventors: Takao Iwasaki; Higashi Ito; Seiichi Watanabe, all of Ohmi, Japan

[73] Assignee: Denki Kagaku Kogyo Kabushiki Kaisha, Tokyo, Japan

[21] Appl. No.: 174,260

[22] Filed: Jul. 31, 1980

Related U.S. Application Data

[63] Continuation of Ser. No. 37,780, May 10, 1979, abandoned.

[51] Int. Cl.³ ............................................. C07C 17/34
[52] U.S. Cl. .................................................... 570/229
[58] Field of Search ................................. 570/226, 229

[56] References Cited

U.S. PATENT DOCUMENTS 3,079,446 2/1963 McFarlane .......................... 260/655
3,755,476 8/1973 Crary et al. .......................... 570/229
3,965,203 6/1976 Smith .................................. 260/655
3,978,146 8/1976 Ohorodnik et al. ................ 260/655

FOREIGN PATENT DOCUMENTS 116306 10/1978 Japan ................................... 570/229
1197539 7/1970 United Kingdom ................ 260/655

Primary Examiner—Charles F. Warren
Assistant Examiner—Joseph A. Boska
Attorney, Agent, or Firm—Oblon, Fisher, Spivak, McClelland & Maier

[57] ABSTRACT

Chloroprene is produced by reacting 3,4-dichlorobutene-1 in an aqueous solution of an alkali metal hydroxide in the presence of at least one of furfuryl alcohol and tetrahydrofurfuryl alcohol preferably at 20° to 70° C.

9 Claims, No Drawings

PROCESS FOR PRODUCING CHLOROPRENE

This is a continuation of application Ser. No. 037,780, filed May 10, 1979, abandoned.

BACKGROUND OF THE INVENTION

1. Field of the Invention

The present invention relates to a process for producing chloroprene. More particularly, it relates to a process for producing chloroprene by reacting 3,4-dichlorobutene-1 in an aqueous solution of an alkali metal hydroxide to result a dehydrochlorination.

2. Description of the Prior Arts

Chloroprene can be produced by chlorinating excess of butadiene to prepare a reaction mixture containing 3,4-dichlorobutene-1 and 1,4-dichlorobutene-2 and separating the unreacted butadiene and isomerizing 1,4-dichlorobutene-2 to 3,4-dichlorobutene-1 and converting 3,4-dichlorobutene-1 to chloroprene by reacting 3,4-dichlorobutene-1 in an aqueous solution of a base to result a dehydrochlorination. However, 1-chlorobutadiene-1,3 is usually formed as a by-product in the dehydrochlorination.

It has been well-known to result a dehydrochlorination of 3,4-dichlorobutene-1 in an aqueous solution of a base. The chloroprene obtained by such conventional process, usually contains 2 to 3 wt.% of 1-chlorobutadiene-1,3. Accordingly, it has been known that physical properties of the polymer produced by using such chloroprene containing 1-chlorobutadiene-1,3 are inferior.

As well-known, boiling points of chloroprene and 1-chlorobutadiene-1,3 at the atmospheric pressure are respectively 59.4° C. and 68.4° C. In order to separate them, highly precision distillation is required. Moreover, a residence time of chloroprene in a precision distillation tower is long so as to cause easily a popcorn polymerization of chloroprene during the distillation step whereby it is difficult to obtain chloroprene having high purity in an industrial process.

In order to overcome such disadvantages, it has been proposed to add an organic solvent to the aqueous solution of a base. However, a satisfactory result could not be obtained.

For example, in Japanese Examined Patent Publication No. 25054/1967, ethyl alcohol is added in the reaction at 70° C. whereby about 1% of 1-chlorobutadiene-1,3 is formed as the by-product. In Japanese Unexamined Patent Publication No. 106907/1975, propanol-2 is added in the reaction at 71° C., whereby 1.2% of 1-chlorobutadiene-1,3 is formed as the by-product. In Japanese Examined Patent Publication No. 20283/1970, dimethylsulfoxide is added in the reaction and there is no description of 1-chlorobutadiene-1,3. In U.S. Pat. No. 3,079,446, an ether alcohol or a water soluble cyclic ether is added in the reaction. However high reaction temperature such as 80° to 120° C. is required whereby it is considered to form relatively large amounts of the polymer and 1-chlorobutadiene-1,3 as the by-product.

SUMMARY OF THE INVENTION

It is an object of the present invention to provide a process for producing chloroprene by improving a contact of an aqueous solution of a base with 3,4-dichlorobutene-1 by adding an organic solvent in a reactor to increase the reaction velocity.

It is another object of the present invention to provide a process for producing chloroprene having high purity by reducing a polymerization of chloroprene and a formation of a by-product of 1-chlorobutadiene-1,3 in the reaction of the dehydrochlorination by reacting at relatively low temperature of near the room temperature.

The foregoing and other objects of the present invention have been attained by reacting 3,4-dichlorobutene-1 in an aqueous solution of an alkali metal hydroxide in the presence of at least one of furfuryl alcohol and tetrahydrofurfuryl alcohol preferably at 20° to 70° C. to result a dehydrochlorination.

DETAILED DESCRIPTION OF THE PREFERRED EMBODIMENTS

In the process of the present invention at least one of furfuryl alcohol and tetrahydrofurfuryl alcohol is added as the organic solvent to impart the effect of the present invention.

In the reaction a concentration of an aqueous solution of an alkali metal hydroxide can be at high concentration such as 30 to 50 wt.% whereby a recovery of an alkali metal chloride as the by-product is easily obtained.

In the process of the present invention, the reaction temperature is preferably in a range of 20° to 70° C. When it is lower than 20° C., the reaction velocity is slow to be uneconomical. The reaction velocity can be improved by increasing a ratio of the solvent at certain level. However, in view of equipments and energy for the recovery of the solvent, the increase of the ratio of the solvent is uneconomical.

When it is higher than 70° C., the amount of 1-chlorobutadiene-1,3 as the by-product is increased and the polymerization of 3,4-dichlorobutene-1 is easily caused in the reactor. It is especially preferable to react it at 25° to 50° C.

Furfuryl alcohol and/or tetrahydrofurfuryl alcohol can be charged in the reactor by itself or with 3,4-dichlorobutene-1. A ratio of furfuryl alcohol and/or tetrahydrofurfuryl alcohol to 3,4-dichlorobutene-1 is usually in a range of 0.1 to 6 by volume preferably 0.5 to 4 by volume.

The base is preferably an alkali metal hydroxide. When a concentration of the base is about 10 wt.%, the reaction velocity is slow. When a concentration of the base is in a range of 20 to 50 wt.% especially 30 to 50 wt.%, the reaction velocity is fast. In view of the recovery of the metal chloride and the treatment of wasted water, higher concentration is economically advantageous.

The base is used at more than stoichiometric equivalent required for the dehydrochlorination of 3,4-dichlorobutene-1, especially at 1.1 to 1.2 times of the stoichiometric equivalent.

The reaction pressure is economically the atmospheric pressure however, it is possible to perform the reaction at an elevated pressure or a reduced pressure, if necessary.

In order to inhibit the polymerization of chloroprene, it is possible to add phenothiazine, 4-tert-butyl catechol or hydroquinone, etc.

The process of the present invention is summarized as follows.

In the production of chloroprene by a dehydrochlorination of 3,4-dichlorobutene-1 in an aqueous solution of a base, furfuryl alcohol and/or tetrahydrofurfuryl alcohol is added to increase the reaction velocity.

The reaction can be performed at relatively low temperature near the room temperature.

The amount of 1-chlorobutadiene-1,3 as the by-product can be small whereby a precision distillation is not required.

The reaction is performed at low temperature whereby the polymerization of chloroprene is not substantially caused.

The aqueous solution of the base having high concentration can be used whereby the recovery of the metal chloride is easily performed. These advantages are given by the process of the present invention.

The present invention will be further illustrated by certain examples and references which are provided for purposes of illustration only and are not intended to be limiting the present invention.

In Table, the following symbols are used;
CP: 2-chlorobutadiene-1,3 (chloroprene)
1-CP: 1-chlorobutadiene-1,3
DCB: 3,4-dichlorobutene-1
FA: furfuryl alcohol
THFA: tetrahydrofurfuryl alcohol
IA: isopropyl alcohol

REFERENCES 1–3

In accordance with the process of the example except using the other solvent or no solvent, the reaction and the test were carried out.

When the conversion was too low, the amount of 1-chlorobutadien-1,3 as the by-product is not shown because of difficulty of the analysis.

TABLE 1

| No. | Solvent | Reaction temperature (°C.) | Solvent/DCB (vol.) | Reaction time (min.) | Product (mole %) CP | 1-CP | DCB | Conversion (%) | $\frac{1\text{-}CP}{CP} \times 100$ (%) |
|---|---|---|---|---|---|---|---|---|---|
| Exp. 1 | FA | 30 | 4 | 10 | 50.81 | 0.30 | 48.89 | 51.1 | 0.59 |
|  |  |  |  | 20 | 58.09 | 0.35 | 41.56 | 58.4 | 0.60 |
|  |  |  |  | 60 | 74.41 | 0.47 | 25.12 | 74.9 | 0.63 |
| Exp. 2 | THFA | 60 | 0.5 | 20 | 87.62 | 0.40 | 11.98 | 88.0 | 0.46 |
|  |  |  |  | 40 | 94.73 | 0.41 | 4.86 | 95.1 | 0.43 |
|  |  |  |  | 60 | 96.47 | 0.42 | 3.11 | 96.9 | 0.44 |
| Exp. 3 | THFA | 30 | 1 | 5 | 80.06 | 0.18 | 19.76 | 80.2 | 0.22 |
|  |  |  |  | 20 | 91.08 | 0.20 | 8.72 | 91.3 | 0.22 |
|  |  |  |  | 60 | 97.13 | 0.22 | 2.65 | 97.4 | 0.23 |
| Exp. 4 | THFA | 30 | 0.5 | 10 | 72.98 | 0.14 | 26.88 | 73.1 | 0.20 |
|  |  |  |  | 20 | 78.60 | 0.15 | 21.25 | 78.8 | 0.19 |
|  |  |  |  | 60 | 86.85 | 0.18 | 12.97 | 87.0 | 0.20 |
| Ref. 1 | IA | 30 | 1 | 10 | 3.72 |  | 96.28 | 3.7 | — |
|  |  |  |  | 20 | 5.97 | 0.01 | 94.02 | 6.0 | — |
|  |  |  |  | 60 | 14.20 | 0.02 | 85.78 | 14.2 | — |
| Ref 2 | IA | 70 | 4 | 10 | 37.01 | 0.34 | 62.65 | 37.4 | 0.91 |
|  |  |  |  | 20 | 47.80 | 0.40 | 51.80 | 48.2 | 0.84 |
|  |  |  |  | 60 | 76.47 | 0.64 | 22.89 | 77.1 | 0.84 |
| Ref. 3 | none | 70 | — | 10 | 0.33 |  | 99.67 | 0.3 | — |
|  |  |  |  | 20 | 0.61 |  | 99.39 | 0.6 | — |
|  |  |  |  | 60 | 1.80 | 0.02 | 98.18 | 1.8 | — |

EXAMPLES 1–4

In a 500 ml four necked flask equipped with a stirrer, an aqueous solution of sodium hydroxide and furfuryl alcohol or tetrahydrofurfuryl alcohol were added. The mixture was stirred and heated to the specific reaction temperature. Then, 3,4-dichlorobutene-1 was gradually added under maintaining the specific reaction temperature by cooling with water to prevent the elevation of the temperature caused by the reaction heat or heating with hot water.

When all of 3,4-dichlorobutene-1 was charged, it is considered as the initiation of the reaction. The minimum amount of each sample required for a gas chromatography was sampled for each specific time from the initiation of the reaction. The sample was extracted with water and the oil phase was analyzed by the gas chromatography. In the reactor, any polymerization inhibitor was not added.

The details of the reaction conditions are shown in Table 1. The common reaction conditions were as follows. The concentration of the aqueous solution of sodium hydroxide of 30 wt.%; The molar ratio of sodium hydroxide to 3,4-dichlorobutene-1 of 1.2. The charged amounts of the materials were controlled to be about 450 ml in each example since the level in the reactor affects to the stirring efficiency.

What is claimed is:

1. A process for producing chloroprene, comprising: reacting 3,4-dichlorobutene-1 with a base in an aqueous solution in the presence of tetrahydrofurfuryl alcohol at a temperature of 20° to 70° C.

2. The process of claim 1, wherein said base is an alkali metal hydroxide.

3. The process of claim 1, wherein said base is present in a quantity in excess over the stoichimetric eqivalent of 3,4-dichlorobutene-1.

4. The process of claim 3, wherein said excess amount of base ranges from 1.1 to 1.2 times the stoichimetric equivalent of said 3,4-dichlorobutene-1.

5. The process of claim 1, wherein the concentration of said base in said aqueous solution is within the range of 20 to 50 weight %.

6. The process of claim 5, wherein said concentration of base ranges from 30 to 50 weight %.

7. The process of claim 1, wherein the ratio of said tetrahydrofurfuryl alcohol to said 3,4-dichlorobutene-1 ranges from 0.1 to 6 by volume.

8. The process of claim 7, wherein said ratio ranges from 0.5 to 4 by volume.

9. The process of claim 1, wherein said reaction is conducted in the presence of a polymerization inhibitor selected from the group consisting of phenothiazine, 4-t-butyl-catechol and hydroquinone.

* * * * *